United States Patent [19]
Rilliet

[11] 4,434,802
[45] Mar. 6, 1984

[54] BLOOD COLLECTION UNIT

[75] Inventor: Francois Rilliet, Geneva, Switzerland

[73] Assignee: Dematex Development & Investment Establishment, Vaduz, Liechtenstein

[21] Appl. No.: 400,711

[22] Filed: Jul. 22, 1982

Related U.S. Application Data

[63] Continuation-in-part of Ser. No. 233,168, Feb. 10, 1981, abandoned.

[30] Foreign Application Priority Data

Jan. 21, 1982 [EP] European Pat. Off. ............ 82200074

[51] Int. Cl.³ .............................................. A61B 5/14
[52] U.S. Cl. .................................................... 128/764
[58] Field of Search ................ 128/763, 764, 765, 766

[56] References Cited

U.S. PATENT DOCUMENTS

| | | | |
|---|---|---|---|
| 3,814,079 | 6/1974 | Le Roy, Sr. ........................ | 128/764 |
| 3,930,492 | 1/1976 | Hatsuno et al. ..................... | 128/764 |
| 4,020,831 | 5/1977 | Adler .................................. | 128/765 |
| 4,066,067 | 1/1978 | Micheli .............................. | 128/764 |

FOREIGN PATENT DOCUMENTS 2357885  3/1978  France ................................. 128/765

*Primary Examiner*—John D. Yasko
*Attorney, Agent, or Firm*—Robert E. Burns; Emmanuel J. Lobato; Bruce L. Adams

[57] ABSTRACT

A blood collection unit has a primary tube of narrow bore hermetically and concentrically assembled to a secondary tube of larger diameter either by a plunger attached to the primary tube and on which the secondary tube is slidably mounted, or by the skirt of a stopper closing both tubes. One of the tubes is closed by a stopper of fitting-over form, the two tubes forming a closed communicating space into which a blood sample is introduced through a double ended needle, passing into one of the tube prior to passing into the other tube. For sedimentation rate determinations, the plunger system can be operated either with or without the closed communicating space under vacuum. Progressive entry of blood into the system is controlled by the narrow bore primary tube.

17 Claims, 12 Drawing Figures

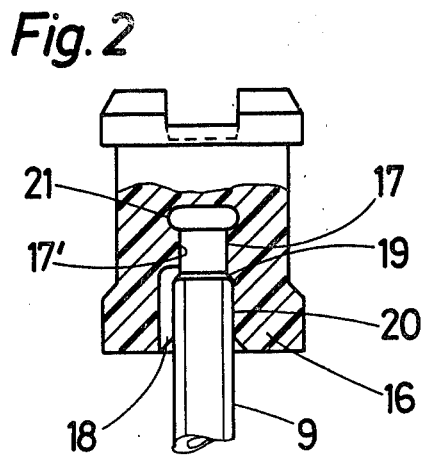

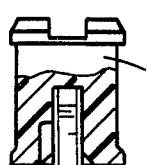
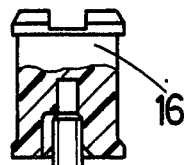
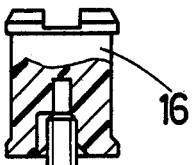
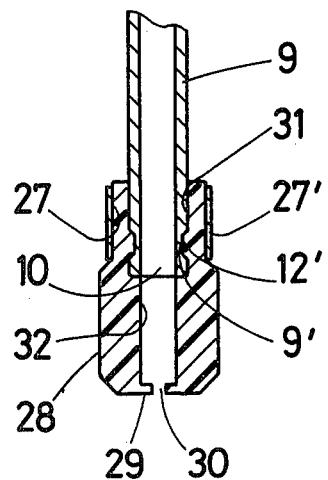
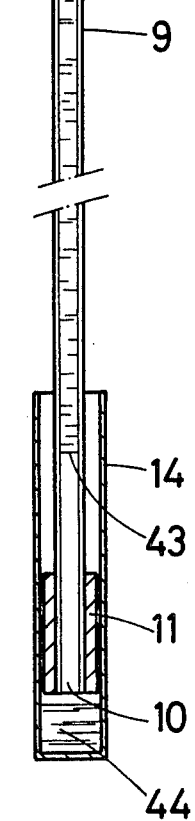
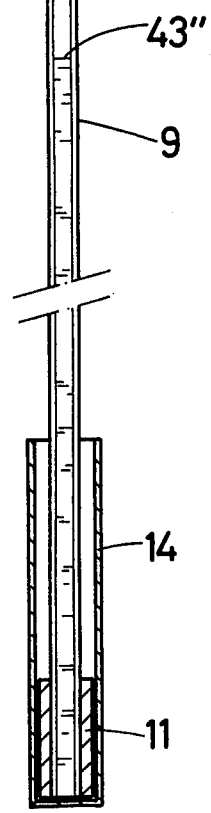

BLOOD COLLECTION UNIT

RELATED APPLICATION

This application is a continuation-in-part of application Ser. No. 233,168, filed Feb. 10, 1981, now abandoned.

BACKGROUND OF THE INVENTION

The invention relates to blood collection systems particularly, but not exclusively, those of the type comprising an evacuated blood-collection tube closed by a stopper and an open, tubular double-ended needle holder slidably mounted on the tube or its stopper. This needle holder carries a hollow needle having one part protruding axially from the closed end of the holder, for pricking into a vein, and another part extending axially within the holder, the latter part being encased in a loose, flexible cover or sleeve. To take a blood sample, the needle is pricked into a vein and the evacuated tube displaced until the needle pierces the stopper membrane, so that blood is sucked into the evacuated tube.

However, in practice, conventional evacuated blood sampling systems are often difficult to use or have shortcomings that create health hazards for laboratory staff and may alter the results of some blood determinations. This is particularly the case with samples collected for determinations of the blood sedimentation rate, using standardized sedimentation pipettes known as the Westergren or the Wintrobe types. The Westergren is characterized by a narrow, 2.5 bore, an outer diameter of 5.5 mm and a length of 25 to 27 mm. Filled with blood and placed on a rack, they allow reading of the rate of sedimentation of blood cells for a given sample of blood.

The difficulty stems mainly from the need to open the collection tube in order to introduce the sedimentation pipette in it and to transfer the sample either by sucking it (mouth pipetting) or by mechanical means, such as electric pumps.

New devices have been proposed with a cylindrical washer or plunger set at one end of the pipette. These pipettes are introduced into the collection tube after opening, the peripheral wall of the plunger sliding tightly against the inner wall of the tube. The pipette is lodged in a central bore in the plunger. At the bottom end of the plunger is a type of slotted membrane which acts as a valve so that when the pipette is pushed down the collection tube, blood raises into its bore up to a determined level.

All these devices have in common the drawback of necessitating opening of the collection tube. This creates concern to the laboratory staff as the blood samples with which such determinations are made have a higher than the average contamination risk, e.g. viral hepatitis.

Furthermore with the above mentioned pipettes having a cylindrical plunger, there is a risk of air bubbles forming in or being transferred into the pipettes, with possible alteration of the results. Owing to this factor, their handling calls for rather careful and lengthy operations, not appropriate when a high number of tests is involved.

Another shortcoming of evacuated tubes is the well known fact that due to the vacuum in the tubes, blood gushes out of the needle in a narrow parallel jet with an exaggerated speed and strength, breaking against the tube inner wall and entailing an alteration of the blood cells which may affect certain determinations, among which coagulation and sedimentation rates are the most vulnerable ones.

SUMMARY OF THE INVENTION

An object of the invention is to provide a new blood collection system which obviates advantageously the problem of damage made to the cells at the entry into conventional evacuated tubes for coagulation, sedimentation and all other associated tests and may also obviate the mentioned problems associated with blood sedimentation tests.

The invention therefore provides a blood collection unit, for use in connection with a tubular needle-holder carrying a double-ended hollow needle extending coaxially within the holder, the unit comprising:

a primary tube having first and second open ends and a narrow bore able to receive the needle;

a secondary tube of considerably larger diameter than the primary tube and considerably greater volumetric capacity than the primary tube, the secondary tube having at least one open end;

the narrow bore of the primary tube having a diameter (typically 2 to 2.5 mm) which is significantly closer to the diameter of the needle bore (typically 0.5 to 0.8 mm) than to the inner diameter of the secondary tube (typically 10.5 to 14 mm), the difference of the primary tube narrow bore diameter and the needle bore diameter being such (typically 1.5 to 1.7 mm) that when blood enters the primary tube from the needle a peripheral lateral attraction is produced on the blood flux which comes to fully occupy the primary tube narrow bore, the length of the primary tube being at least $2D+1$ where D is the inner diameter of the secondary tube and l is the length of the needle which is penetrable in the primary tube;

a stopper having a skirt sealably fitting over and around an open end of one of the two tubes and a sealing membrane closing the end of the tube;

means concentrically connecting the primary and secondary tubes whereby at least one open end of the primary tube is enclosed in the secondary tube, the unit forming a closed communicating space for the collection of blood and said open end of the primary tube having a free passageway such that a complete blood suspension including liquid and solid phases can pass from one tube to the other.

In one embodiment, the stopper sealably fits over and around the first end of the primary tube, the primary and secondary tubes being connected by an annular sleeve which sealably engages with an inside surface of the secondary tube and an outside surface of the primary tube on which it is preferably set adjacent its second and so as to form a plunger on which the secondary tube is slidably mounted. In this embodiment, initial filling of the primary tube may be obtained either with a pre-existing vacuum inside the unit or by the effect of a similar depression created by sliding the secondary tube outwardly over the plunger when the inside pressure in the closed communicating space is in equilibrium with the outside atmosphere. Also, the stopper is preferably movably mounted on the first end of the primary tube between a sealing position and a venting position communicating the interior of the primary tube with the exterior, whereby when blood has been delivered through the stopper membrane to the primary tube the blood may be transferred to the secondary tube by placing the stopper in the venting position and sliding the secondary tube outwardly in relation to the second end of the primary tube, to a blood-receiving position.

Also, the secondary tube of the evacuated unit contains an anticoagulating agent which is mixed with blood delivered from the primary tube when the secondary tube is slid to said blood-receving position while the stopper is in the venting position, the secondary tube being slidable inwardly in relation to the second end of the primary tube to a position in which the blood and anticoagulating agent are transferred into the primary tube up to an intermediate level of the primary tube extending beyond the open end of the secondary tube.

With this unit, it is possible to collect the blood sample, prepare the reading sedimentation pipette (formed by the primary tube), and obtain the results of the sedimentation rate tests without having to open the collection tubes, thus providing a completely closed system preferable for the hygiene of both laboratory and medical departments.

It eliminates the problem of transfer or formation of bubbles in the reading pipettes. It simplifies and shortens the testing procedure significantly. Also it minimizes the damage caused to the blood cells at the entry into the unit as blood enters the primary tube in the form of a liquid column with a well controlled progressive flow.

The unit is used to collect the sample in the same way as conventional evacuated tubes are used. The stoppered end of the primary tube is introduced into a needle holder. One end of the needle penetrates the stopper membrane whilst the other end is in the vein. The liquid column enters the primary tube until the complete vacuum is filled.

The primary tube stopper is then set in the venting position and a depression is created in the secondary tube by pulling it slightly outwards from its original position, sliding it over the primary tube plunger. The total content of the primary tube is thus transferred into the secondary tube containing the anticoagulant. The two liquids are mixed and homogeinized. Then the sample is pushed upwards and reintroduced into the primary tube by sliding the secondary tube over the plunger towards the primary tube. The unit is set on a reading rack and left to sediment. If reading is to take place in a laboratory remote from the place of collection, then after homogeinization the unit will be sealably restoppered; transfer from the secondary to the primary tube and consecutive reading will then be performed in the laboratory.

However, in a modified form of the above-described embodiment, the larger diameter secondary tube has a second open end sealably closed by a second stopper through which blood can be introduced via the hollow needle of the needle-holder directly into the secondary tube and hence immediately into contact with the anticoagulant. In this form of the embodiment, the operator will therefore have an alternate solution for introducing blood into the system; either through the narrow bore primary tube if the transfer to the secondary tube will be done shortly afterwards, or directly into the large diameter secondary tube if the transfer will be delayed. After direct filling of the large diameter secondary tube, subsequent operations for transferring the mixed specimen will be identical to the ones previously described, as the configuration of the closed communicating spaces is identical.

In another embodiment of the invention, the stopper skirt sealably fits over and around the open end of the secondary tube, the primary tube being at least substantially entirely contained within the secondary tube and extending usually over at least ½ the length of the secondary tube. In this case, the stopper assembles the primary and secondary tubes as one unit. In the same manner as for the previously described system, the blood sample is introduced firstly into the primary tube when the double ended needle penetrates the stopper membrane and, after the controlled entry of the blood flux, the blood gently drips into the secondary tube. The primary tube may be attached to the stopper membrane or may be supported by a separate circular flexible piece forming a separate piece from the main body of the stopper.

Thus, in both embodiments, the narrow-bore primary tube acts on the thin parallel jet of blood gushing from the needle by a peripheral lateral attraction to convert it into a relatively slow and well-controlled flow fully occupying the primary tube bore, thereby avoiding damage to the blood cells as the complete blood suspension passes into the secondary tube.

BRIEF DESCRIPTION OF DRAWINGS

FIGS. 1 to 8 schematically show a first embodiment of the invention and variations thereof.

FIG. 1 shows a blood-collection unit according to the invention assembled with a needle holder.

FIGS. 2 and 3 show preferred types of stopper incorporating a venting system, mounted on one end of the primary tube, the stopper of FIG. 3 having a special head cooperating with the flexible needle-covering sleeve of a needle holder.

FIG. 4 shows a modified type of plunger mounted on the other end of the primary tube.

FIGS. 5 to 7 illustrate operation of the first embodiment for carrying out a blood sedimentation rate determination.

FIG. 8 shows a variation of the first embodiment used for carrying out a sedimentation rate determination.

DESCRIPTION OF PREFERRED EMBODIMENTS

Figure 8:
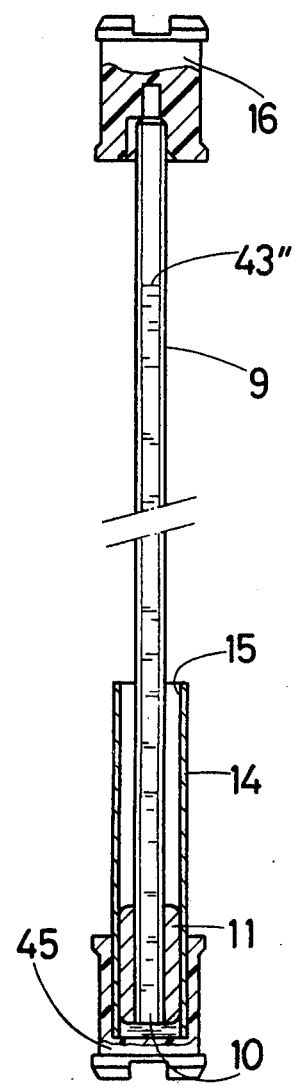

The unit of FIG. 1 comprises a primary tube 9 with a narrow bore 8 made to the specifications of the Westergren, Wintrobe or other types of sedimentation pipettes. Tube 9 is closed at one end by a stopper 4 that fits over and around the tube neck, as opposed to the "fitting in" stoppers used on conventional evacuated tubes. Stopper 4 consists of a hollow generally cylindrical body of deformable material, such as synthetic rubber, having a head 5 including a sealing membrane 6 and an integral skirt 7 extending from the head. The skirt 7 is adapted to fit over and around the end 13 of tube 9, so that the membrane 6 closes the open end of the tube.

At its opposite end 10, the primary tube 9 is force fitted in a cylindrical sleeve or plunger 11, of which the peripheral wall 12 tightly seals against the inner wall 15 of a secondary tube 14, the interiors of the primary and secondary tubes preferably forming a communicating evacuated space. The central bore 19 of plunger 11 tightly grips the primary tube 9 whereas the secondary tube 14 can be slid over the plunger 11, either inwardly towards the stoppered end 13 of the primary tube 9 or outwardly. The secondary tube 14 contains an anticoagulant solution 44.

The stopper 4 of the unit is set inside a tubular holder 1 carrying a double-ended needle 2a, 2b. The end 2b of the needle is covered with a rubber sleeve 3 acting as a multi-sample needle valve. To take a blood sample, the end 2a of the needle is pricked in a vein, and the unit is pushed fully into the holder 1, as shown in FIG. 1, so that the needle end 2b punctures the membrane 6 and blood is sucked into the primary tube 9. It should be noted that the outer surface of the stopper skirt 7 closely fits inside the tubular holder 1 and accurately guides the needle end 2b into the centre of the narrow bore of the primary tube 9. As shown in FIG. 5 a blood column forms at the entry of the primary tube 9 and, once the vacuum has been filled, stops before it reaches the opposite end 10, with a cushion of residual air remaining in the end 10.

FIG. 2 shows a preferred form of stopper 16 of the type described in U.S. Pat. No. 4,204,606, in which an axial venting channel or groove 18 is provided in the inner skirt. The skirt inner wall is split into two cylindrical portions, an upper one 17, and a lower one 20. The lower portion 20 has a slightly enlarged diameter compared to the adjacent upper portion 17, and the two portions are connected by a slanted section 19. The upper portion 17 constitutes, between the top of the axially-directed groove 18 and an upper annular groove 21, a tight sealing zone 17'. This structure provides a pulled-out venting position (shown in FIGS. 2 and 6) and a pushed-in sealing position (shown in FIG. 5).

After placing the stopper 16 in the venting position, with the primary tube rim lying against the slanted section 19, the secondary tube 14 can be pushed outwards over the cylindrical plunger 11 or inwards while the unit remains assembled. This structure providing venting means will also considerably facilitate automated production in manufacturing.

FIG. 3 shows another form of stopper 22 closing the primary tube 9. This stopper has a hollow head and incorporates a chamber 23 closed by a flexible outer end wall 24, in which there is a central slot 26 defined between two flexible lips 25a, 25b extending radially inwardly. Several stoppers of this type are described in U.S. Pat. No. 4,066,067. By virtue of this particular head configuration, the blood collection unit can be inserted into the holder 1 and retained therein through the mere resilient pressure produced between the flexible lips 25a, 25b of the stopper and the rubber sleeve 3. Through this particular structure, the two-tube unit will be held inside the holder 1 as a pre-assembled unit. It will no longer be necessary to prepuncture the stopper membrane 6 which is the usual and tedious technique with conventional systems. Yet the unit will be strongly assembled with the needle holder by this pressure, such that it will not fall out of the holder 1 even held vertically. For the phlebotomist, particularly for these longer two-tube units, the system is made easier to handle and time saving.

Furthermore, this stopper head configuration provides improved means to set the unit inside the holder 1 in the perfect axis of the needle. It will be obvious, considering the small inside bore (2–5 mm) of the primary tube 9, that if the tube 9 is set in the holder 1 at an angle in relation to the needle axis, after the needle punctures the membrane 6, it could miss the tube opening. However, the contact engagement between the stopper lips 25a, 25b and the sleeve 3 will improve guiding of the needle and keep it in alignment with the primary tube entry.

In FIG. 4, the end 10 of primary tube 9 penetrates the plunger bore 31 only partly until it reaches a narrower section 32. The peripheral wall of the plunger has an upper part 27 of smaller outer diameter than a lower part 28, and an annular ring 27' is set by force around the part 27. At its lower end 10, the primary tube 9 has in its outside surface a notch 9', in which a corresponding rib 12' of the plunger fits. The lower bore section 32 of the plunger is provided with a thin membrane 29 having a slotted opening 30 which may, as shown, provide a permanent opening or may form a pressure-actuated valve; in either case there is a passageway for the complete blood suspension including liquid and solid phases of the blood sample. The provision of a slotted membrane or other temporary closure device is particularly recommended when the primary tube is graduated for the sedimentation-rate reading, in which case the blood column has to be brought to the graduated level leaving some residual blood in the secondary tube 14.

When blood flows out of a vein, it rapidly coagulates in a solid mass known as a clot. To allow sedimentation to occur this phenomenon must be prevented and to this end the sample will be mixed with an anticoagulant solution, as rapidly as possible. Owing to the small bore of the primary tube 9 it is not possible to achieve mixing of the blood sample and an anticoagulant inside the primary tube. This mixing is therefore carried out in the secondary tube which contains anticoagulant 44.

Handling is simple, hygienic and rapid. FIG. 5 shows the primary tube 9 after it has been filled with blood and removed from the holder 1, the blood column having stopped at level 43 in the primary tube 9 which exerts a sufficient surface effect on the blood to hold the inverted column static. By placing the stopper 16 in the venting position and pulling the secondary tube 14 outwardly, a short distance over the plunger 11, a depression is created inside the tube 9 by which the blood sample is smoothly transferred into the secondary tube 14 and mixes with the anticoagulant solution up to a level 43', FIG. 6.

After homogenization, the secondary tube 14 is pushed inwardly over the plunger 11 as shown in FIG. 7, and the mixed sample is transferred into the primary tube 9 up to a level 43'' extending well beyond the open end of the secondary tube 14. The unit is then set on a reading rack with the top of the blood column at the level 43' of a zero graduation of a graduated reading scale.

Once the primary tube is filled and set for the test, the bore produces a peripheral surface effect on blood as it stands static. The 2.5 mm bore affects the blood viscosity as a constant and standard factor for the fall of cells by sedimentation.

If desired, the inner surface of tube 14 can be provided with stops for limiting the penetration of plunger 11 in the tube 14.

By introducing blood into the evacuated tube system through a narrow bore primary tube 9 before it reaches the standard diameter secondary tube 14, the problems of turbulence and bubbles are eliminated.

FIG. 8 shows a variation of the first embodiment in which the larger-diameter secondary tube 14 has, opposite its end receiving the plunger 11, a second open end closed by a stopper 45. The stopper 45 may be similar to the previously-described stoppers, with appropriate dimensional modifications to fit on the tube 14 whereas its outer dimensions will be such that it can slidably fit in the needle holder 1 of FIG. 1. The stopper 45 may incorporate a venting system as previously described, but this is not necessary. With the arrangement of FIG. 8, the operator will have the choice of introducing blood either through the stopper 16 into the narrow bore primary tube 9 (i.e. as described previously) or, as shown in FIG. 8, via the stopper 45 into the wider secondary tube 14. The latter mode of use will be chosen if it is known that the subsequent operations will be delayed. When the blood is introduced as shown in FIG. 8, although there will no longer be the advantage of controlled flow entry provided by the narrow bore tube, all of the other advantages of hygiene and rapidity of the system will be maintained and in particular at no time will the collection tube assembly have to be opened.

With the embodiment of FIGS. 1–8, the sucking in of blood through the hollow needle 2b will either be produced by a pre-existing vacuum in an evacuated assembly, or by a depression created by sliding the secondary tube 14 outwardly over the plunger 11.

Figure 9:
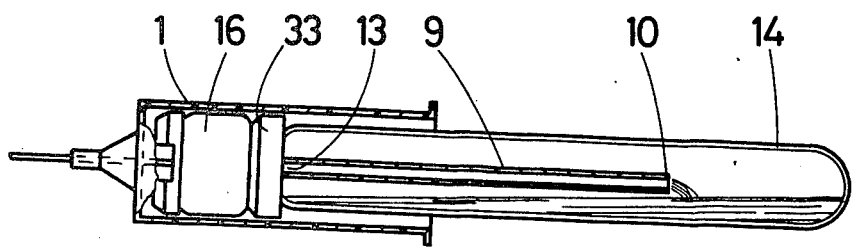
FIG. 9 schematically shows a second embodiment of the invention.

FIG. 9 shows another embodiment in which the primary tube 9 is totally contained within the secondary tube 14. The same stopper 16 fits over and around the secondary tube 14 and assembles the primary and secondary tubes as a unit. In this embodiment, the system extends the benefit of the small bore primary tube controlled flow entry to other blood determinations and particularly coagulation. Inside this narrow bore primary tube 9, blood forms into a liquid column by capillary contact. Flow of this column is controlled by contact with the total peripheral surface of the bore which it completely occupies. At the end of the primary tube blood drips gently into the secondary tube. This is quite different from blood being projected against the tube wall in conventional evacuated tubes. However, the bore of the primary tube as well as its shape and its length can obviously be varied compared to the specific type of primary tube used in the previously described embodiment for sedimentation rate measurements. Particularly the bore at the end 10 could be restricted compared to the other end. The tube 9 could be slightly curved and the bore surface should be non-wettable so as to prevent activation of coagulation factors.

Figure 10:
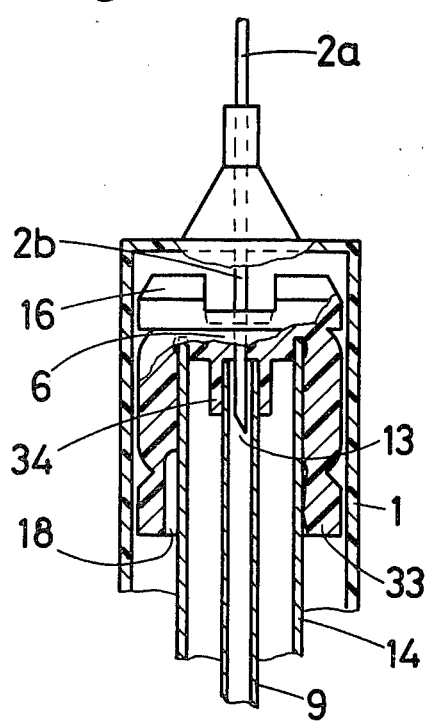
FIGS. 10, 11 and 12 show variations of the stopper of the second embodiment.

With this second embodiment of the unit, the stopper will have a fitting over form as previously described, so that the stopper 16 has, as shown, an integral skirt 33 which sealably fits over the neck of the secondary tube 14 and is advantageously provided with a venting system (e.g. the groove or channel 18 as shown in FIG. 10).

In FIG. 10, when the unit is introduced within the holder 1, the needle 2b penetrates the membrane 6, reaching the primary tube opening 13. Blood flows into the tube 9 as previously described, that is by forming a liquid column. At the inner end 10 of the primary tube 9 it drips gently into the secondary tube 14 filling it quite progressively, as shown in FIG. 9. As shown in FIG. 10, the stopper membrane 6 may advantageously include an inwardly-extending plug which sealably engages with the inner surface of the secondary tube 14, this plug having a central part in the form of an inner annular sleeve or skirt 34 in which the primary tube 9 is set. It should be noted that the outer skirt 33 extends axially well beyond the inner skirt 34. Of course, other forms of attachment for the primary tube could be made.

This flow control system will now be described in detail. In conventional evacuated tubes, blood cells are damaged and sensitive coagulation factors irreversibly altered when blood gushing out of the needle is projected against the opposite end of the tube with an acceleration resulting from the combined effect of the vacuum and the necessarily small bore of the needle channel. The invention incorporates the primary tube as an intermediary element between the needle and the secondary tube. Thus a needle of, for example, 0.9 mm outer diameter and 0.5 to 0.8 mm bore diameter may be engaged inside the narrow bore of the primary tube (e.g. 2 to 2.5 mm inner diameter), the other end of the primary tube opening into the secondary tube with a 10.5 to 13 mm inner diameter. Immediately after its entry into the narrow-bore primary tube, the blood flux coming out of the needle is deviated laterally from its central course towards the wall of the tube under the effect of a peripheral lateral attraction. The close proximity of the narrow bore to the axially-directed flux permits the following physical phenomenon: the primary tube inner diameter being considerably closer to the needle diameter than to the secondary tube diameter, the force produced laterally on the blood flux is stronger than the central force resulting from the pressure differential created inside the unit. The flux is hence deviated and contacts the wall tangentially at one point. Simultaneously, a peripheral capillary phenomenon is produced by the surface of the bore which spontaneously extends this tangential contact of the blood to its total transverse section. The section of the bore being several times larger than that of the needle channel, the flux loses in speed what it has gained in section, as given by the continuity equation:

$$Acm^2 \times Vml = Constant$$

in which $Acm^2$ is the cross-sectional area of the bore and $Vml$ per second represents the average flow speed. The thin and violent central jet of 0.5 to 0.7 mm diameter is thus converted into a 2 to 2.5 mm diameter well-controlled, progressive liquid column which at the end of the primary tube drips gently into the secondary tube. A superior quality of specimen is obtained.

In this structure, the diameter of the primary tube bore (2 to 2.5 mm) is closer to the needle inner diameter (0.5 to 0.8 mm) than to the secondary tube diameter (10.5 to 14 mm). This difference is approximately 1.5 to 1.7 mm with the needle compared to 8.5 to 11.5 mm with the secondary tube. Furthermore, the two tubes have considerably different volumetric capacities, a 250 microliter to 1.2 milliliter volume for the primary tube against a 5 to 15 ml volume capacity for the secondary tube.

Moreover, there is a direct relation between the length of the primary tube and the drop in pressure produced on the flow. Consequently, the length of the primary tube extending beyond the opening of the needle inside the tube will be proportional to the length and volumetric capacity of the secondary tube as well as to the strength of the depression created inside the unit. For an average length of 75 to 100 mm of the secondary tube, the primary tube length should vary from 50 to 75 mm, i.e. about ⅔ to ¾ and in the extreme will always be at least ½ the length of the secondary tube, the minimum length of the primary tube being given by the formula 2D+1 where D is the inner diameter of the secondary tube and l is the length of the needle which is penetrable in the primary tube (usually 5-15 mm). Also, the primary tube length will usually be 20 to 30 or more times the diameter of its transverse section. When the needle is fully introduced into the primary tube, the portion of the primary tube extending beyond the opening of the needle will generally be longer than the total length of the needle which normally is about 40 mm. Usually, the needle will penetrate 5-15 mm in the primary tube leaving a bore length of 35-70 mm to perform the function of blood flow regulator.

Furthermore, in this second embodiment of the invention, the sealing function of the stopper is dissociated from the function of supporting the primary tube, one being external to the secondary tube whilst the other is internal. Assembly and handling are perfectly easy and safe. No breakage of the thin wall tube nor aerosols will occur. This safety aspect is enhanced by the venting channel system. Secondly the fitting-over form of the stopper provides, over the secondary tube outer wall, a cylindrical peripheral guide surface which is concentric to the primary tube bore, the secondary tube and to the inner wall of the needle holder. This cylindrical peripheral surface is sufficiently axially long to maintain the unit in a straight position inside the needle holder and ensures, whether the secondary tube has a diameter of 13 or 16 mm, that the needle will be in axial alignment with the narrow bore of the primary tube.

Figure 11:
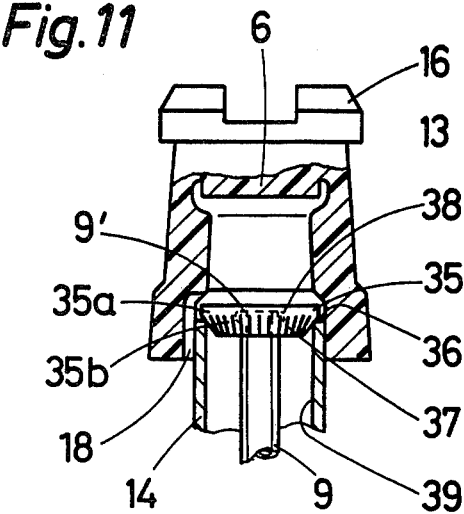

In FIG. 11, the primary tube 9 is attached to a generally circular flexible piece 35 forming a secondary membrane as a separate element of the stopper 16. Owing to its structure and material this piece 35 has a certain resilience. Its peripheral wall has two sections, an upper one 35a and a lower one 35b. The upper section 35a has a diameter equal to or slightly larger than the diameter of the inner neck surface 39 of the secondary tube 14, whilst the lower section 35b is inclined so that its bottom end is smaller in diameter than the tube surface 39 and penetrates into it when the piece 35 lies on the tube rim 36. The piece 35 is provided with a central chamber 38 open at its lower end and in which the head 9' of the primary tube 9 is inserted and held, this chamber 38 being closed by a thin secondary membrane closing the end of tube 9. The lower section 35b is provided with axially-directed venting grooves 37 extending slightly into the upper section 35a until they reach a continuous sealing surface of this upper section.

When the piece 35 lies freely on the tube rim 36, the venting grooves 37 extend slightly above the rim. Instead of axially-directed grooves, equivalent venting means could be provided for communicating the inside of the secondary tube with the exterior when the piece 35 is set on the tube rim. The term axially-directed grooves is intended to include grooves and similar recesses having main axial components to provide the desired venting effect.

For assembling and evacuating the unit, the stopper 16 is set on the secondary tube 14 in the venting position as shown in FIG. 11, the secondary membrane lying on the rim 36. The venting grooves 37 of membrane 35 communicate the inside of tube 14 with the exterior through the venting means in the inner surface of the stopper skirt, namely axially-directed venting groove or channel 18.

When the stopper 16 is pushed fully onto the tube 14 to a sealing position, the piece 35 will be pushed by a protruding part of the main membrane 6 into the neck of tube 14, the continuous part 35a of the peripheral wall creating a tight sealing separation between the stopper and the interior of tube 14. When sampling blood, the needle will penetrate the stopper membrane 6 and the thin membrane of the piece 35 above the chamber 38, thus entering the upper part 13 of the primary tube 9.

Figure 12:
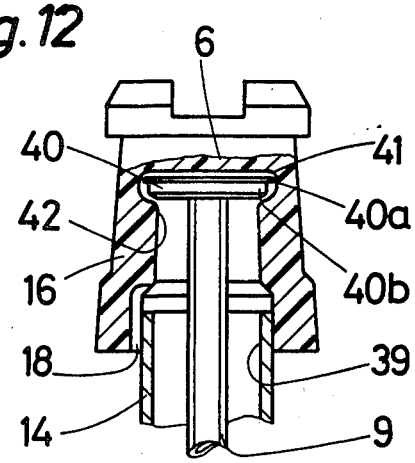

In another variation, FIG. 12, a similar flexible piece 40 forming a secondary membrane is set within an annular groove 41 located in the upper part of the stopper skirt, adjacent the main membrane 6. The membrane-forming piece 40 centrally supports the primary tube 9 with which it may be molded integrally as a single piece. The peripheral wall of piece 40 comprises a rim 40a larger in diameter than the inner skirt diameter 42 so that it is maintained within the annular groove 41, and an adjacent continuous sealing portion 40b equal to or larger in diameter than the tube inner diameter 39 so that when the stopper 16 is pushed on the secondary tube 14 to a tight sealing position, the piece 40 enters the neck of the tube 14 and stands below the stopper, tightly separating the inside of the tube from the stopper.

Further to its function of supporting the primary tube 9, the membrane-forming piece 40 will, after sampling, separate the blood content of the tubes from the stopper. This separation is particularly valuable for analysis in which the contact with the stopper 16 will, for chemical or physical actions alter the sample and bias the results.

After sampling, when the stopper 16 is to be removed from the secondary tube 14 the piece 40 will stay clinched inside the annular groove 41 and therefore will be removed together with the primary tube 9.

Many variations can be made to the above described embodiments. For instance, the circular piece 35 or 40 could, instead of forming a membrane, have an opening communicating with the bore of the primary tube, or the thin secondary membrane of the piece over the end of the primary tube could be slotted. Also the second embodiment need not have a venting system. The secondary tube could also be made with an annular bead on the top of the neck. What is claimed is:

1. A blood-collection unit for use in connection with a tubular needle-holder carrying a double-ended hollow needle extending coaxially within the holder, the unit comprising:

a transparent primary tube having first and second open ends and a narrow bore having a diameter larger than the outside diameter of the needle, said needle extending into said bore;

a transparent secondary tube of considerably larger diameter than the primary tube and considerably greater volumetric capacity than the primary tube, the secondary tube having at least one open end;

the narrow bore of the primary tube having a diameter which is significantly closer to the diameter of the needle bore than to the inner diameter of the secondary tube, the difference of the primary tube narrow bore diameter and the needle bore diameter being such that when blood enters the primary tube from the needle a peripheral lateral attraction is produced on the blood flux which comes to fully occupy the primary tube narrow bore, the length of the primary tube being at least 2D+1 where D is the inner diameter of the secondary tube and l is the length of the needle which is penetrable in the primary tube;

a stopper having a skirt sealably fitting over and around an open end of one of the two tubes and sealing membrane closing the end of the tube;

means concentrically connecting the primary and secondary tubes whereby at least one open end of the primary tube is enclosed in the secondary tube, the unit forming a closed communicating space for the collection of blood and said open end of the primary tube having a free passageway such that a complete blood suspension including liquid and solid phases can pass from one tube to the other.

2. Blood collection unit according to claim 1, in which the stopper sealably fits over and around the first end of the primary tube, the primary and secondary tubes being connected by means of an annular sleeve which sealably engages with an inside surface of the secondary tube and an outside surface of the primary tube.

3. Blood collection unit according to claim 2, in which the secondary tube is slidably mounted on said sleeve, the sleeve being fixed adjacent to the second end of the primary tube.

4. Blood collection unit according to claim 2, in which the stopper is movably mounted on the first end of the primary tube between a sealing position and a venting position communicating the interior of the primary tube with the exterior, whereby when blood has been delivered through the stopper membrane to the primary tube the blood may be transferred to the secondary tube by placing the stopper in the venting position and sliding the secondary tube outwardly in relation to the second end of the primary tube, to a blood-receiving position.

5. Blood collection unit according to claim 4, in which the secondary tube contains an anticoagulating agent which is mixed with blood delivered from the primary tube when the secondary tube is slid to said blood-receiving position while the stopper is in the venting position, the secondary tube being slidable inwardly in relation to the second end of the primary tube to a position in which the blood and anticoagulating agent are transferred into the primary tube up to an intermediate level of the primary tube extending beyond the open end of the secondary tube.

6. Blood collection unit according to claim 2,3,4 or 5, in which said sleeve has a slotted flexible membrane over the second end of the primary tube.

7. Blood collection unit according to claim 2, in which the secondary tube has a second open end sealably closed by a second stopper.

8. Blood collection unit according to claim 7, in which either the first stopper of the primary tube or the second stopper of the secondary tube can be introduced into the tubular needle-holder for the delivery of blood into the respective tube via the hollow needle piercing the respective stopper membrane.

9. Blood collection unit according to claim 1, in which the closed communicating space inside the two tubes is evacuated.

10. Blood collection unit according to claim 1, in which the stopper skirt sealably fits over and around the open end of the secondary tube, the primary tube being at least substantially entirely contained within the secondary tube.

11. Blood collection unit according to claim 10, in which the stopper membrane has an inwardly-extending plug which sealably engages with the inner surface of the secondary tube and has a central annular sleeve in which one end of the primary tube is set.

12. Blood collection unit according to claim 10, in which the stopper skirt includes a venting channel in its inner surface in contact with the secondary tube and is movable on the end of the secondary tube between a pushed-in sealing poaition and a pulled-out venting position, the first end of the primary tube being centrally supported by a circular flexible piece which has a peripheral surface which sealably fits inside the open end of the secondary tube when the stopper is in the pushed-in sealing position.

13. Blood collection unit according to claim 12, in which the circular flexible piece forms a secondary membrane closing the open first end of the primary tube, its peripheral sealing surface being extended by a sloping edge which extends into the open end of the secondary tube and has at least one venting groove communicating the inside of the secondary tube with the exterior when the stopper is in the pulled-out venting position and said sloping edge rests against the end of the secondary tube.

14. Blood collection unit according to claim 12, in which said skirt of the stopper has an annular recess adjacent the stopper membrane, said annular recess housing the circular flexible piece which comprises a peripheral rim having a diameter larger than the inner skirt diameter and an adjacent peripheral sealing surface equal or larger in diameter to the secondary tube inner diameter.

15. Blood collection unit according to claim 12,13 or 14, in which the circular flexible piece comprises a central opening in which the first end of the primary tube is set and a secondary membrane over the open first end of the primary tube.

16. Blood collection unit according to claim 1,2 or 10, in which the stopper skirt has an outer surface defining a cylindrical guide surface coaxial to the centrally supported primary tube, said cylindrical guide surface extending axially beyond an end of the primary tube adjacent to the stopper membrane whereby when the blood collection unit is introduced into the needle holder, the unit is guided by engagement of said guide surface in the needle holder to introduce the bore of the primary tube coaxially about the needle.

17. Blood collection unit according to claim 1, in which said primary tube has in inner diameter of about 2 to 2.5 mm and said secondary tube has an inner diameter of about 10.5 to 13 mm.

* * * * *